United States Patent [19]
Henschel et al.

[11] Patent Number: 5,674,258
[45] Date of Patent: Oct. 7, 1997

[54] PACKAGED INTEGRATED ACCELEROMETER

[75] Inventors: Mark E. Henschel, Phoenix; Juan G. Milla, Mesa; Kelly J. Consoer, Chandler, all of Ariz.; James M. Sikorski, Moundsview, Minn.; Larry R. Larson, Chandler, Ariz.

[73] Assignee: Medtronic, Inc., Minneapolis, Minn.

[21] Appl. No.: 399,072

[22] Filed: Mar. 8, 1995

[51] Int. Cl.⁶ ........................................... A61N 1/365
[52] U.S. Cl. .................. 607/19; 73/514.36; 310/370; 310/340
[58] Field of Search ................. 607/19, 20; 73/514.36, 73/514.38, 514.01, 514.21; 310/370, 344, 340

[56]  References Cited

U.S. PATENT DOCUMENTS

| | | |
|---|---|---|
| 4,140,132 | 2/1979 | Dahl . |
| 4,379,459 | 4/1983 | Stein . |
| 4,476,868 | 10/1984 | Thompson . |
| 4,485,813 | 12/1984 | Anderson . |
| 4,556,063 | 12/1985 | Thompson . |
| 4,653,326 | 3/1987 | Danel . |
| 4,679,434 | 7/1987 | Stewart . |
| 4,742,182 | 5/1988 | Fuchs . |
| 5,014,702 | 5/1991 | Alt . |
| 5,031,615 | 7/1991 | Alt . |
| 5,052,388 | 10/1991 | Sivula . |
| 5,235,237 | 8/1993 | Leonhardt . |
| 5,309,014 | 5/1994 | Wilson . |
| 5,312,453 | 5/1994 | Shelton . |
| 5,315,204 | 5/1994 | Park . |
| 5,315,205 | 5/1994 | Ohno . |

*Primary Examiner*—William E. Kamm
*Assistant Examiner*—Kennedy J. Schaetzle
*Attorney, Agent, or Firm*—Thomas F. Woods; Reed A. Duthler; Harold R. Patton

[57]  ABSTRACT

Disclosed are method and apparatus for creating a cantilever accelerometer beam by mechanically forming an accelerometer from a piezoelectric substrate. The inherent structure of the accelerometer provides a means for employing surface mount technology (SMT), or a protective package may be utilized to couple the accelerometer to the hybrid circuit within an implantable pacemaker. The sensor's structure is defined by three members. The first and second members are used to couple the sensor to the hybrid circuit and the third member defines the cantilever accelerometer beam, which generates an electrical output signal indicative of a patient's activity.

20 Claims, 5 Drawing Sheets

PACKAGED INTEGRATED ACCELEROMETER

BACKGROUND OF THE INVENTION

The present invention relates generally to implantable cardiac pacemakers, and in particular to a method for surface mounting a piezoceramic accelerometer directly to a hybrid circuit thereon within a hermetically sealed pacemaker housing.

Present day piezoceramic cantilevered beams are well understood in the area of cardiac pacing, as well as the equations which govern their characteristics. Conventional electrical and mechanical connection of the beam is typically clamped on the short edge of the beam producing a cantilever configuration, which defines the overall beam length.

U.S. Pat. No. 4,140,132, issued to Dahl describes one of the first uses of piezoceramic material as a physical activity sensor. The issued patent describes an elongated piezoelectric cantilevered element with a weighted mass on one end of the element enclosed within an implanted cardiac pacemaker.

U.S. Pat. No. 5,235,237, issued to Leonhardt discloses a piezoceramic bending beam accelerometer enclosed within a housing and employs surface mount technology for mounting the packaged accelerometer by clamping down one end of the accelerometer within the enclosed package.

U.S. Pat. No. 4,653,326, issued to Danel et al. cites an accelerometer capable of measuring a component of acceleration by means of a variable capacitance capacitor.

U.S. Pat. No. 5,031,615, issued to Alt cites a pacemaker which employs an accelerometer comprising a miniaturized mechanoelectrical converter or transducer formed in a semiconductor device.

However, the aforementioned disclosures have disadvantages. For example, the beam connection to the package or pacemaker shield becomes a dominant factor in determining the sensitivity output of the accelerometer when employing a bonding medium of either solder or conductive epoxy. When bonding, the medium may bleed onto the beam resulting in a reduced effective net length of the beam and an attenuation of piezoceramic sensitivity. Hence, the bonding step can adversely affect the overall beam performance and contribute to manufacturing yield loss. Also, the bonding method, supra, requires complex and expensive packing techniques to ensure a robust design.

SUMMARY OF THE INVENTION

The present invention overcomes the disadvantages of the prior art by providing a method of and apparatus for coupling an accelerometer within a cardiac pacemaker. The way in which this solution is achieved by the invention will be understood by considering the following description.

In a preferred aspect, the present invention provides a cardiac pacemaker with a piezoceramic accelerometer directly coupled to the pacemaker hybrid circuit thereto via surface mount technology, (SMT).

More specifically, the accelerometer crystal is wider than the prior art with two incisions made from the same side thereby forming three members. The outer members are used for coupling the accelerometer crystal to the hybrid circuit and define the inactive areas of the crystal. The third and center member delineates the active area of the crystal, that is, the piezoceramic cantilevered beam which generates an electrical signal based upon patient activity. Unlike the prior art, the invention intregrates the coupling members as part of the accelerometer and renders an accelerometer design independent of the coupling method employed.

In another aspect of the invention, the accelerometer is custom packaged in a metal housing prior to surface mounting to the hybrid circuit. Unlike the inherent disadvantages associated with the prior art, the invention employs a custom package to contact only the outer legs of the accelerometer thereby allowing the entire cantilever beam to move freely within the z-plane of the sensor.

An advantage of the method of the present invention is the outer dimensions can be held constant and the electrical output signal can be mechanically adjusted by the depth and width of the aforementioned incisions, thereby a family of accelerometer crystals of different outputs could employ the same package.

Another advantage of the present invention is the electrical output signal can be further adjusted by the attachment method. That is, by decreasing or increasing the bonding area of the outer members of the hybrid adds or subtracts to the output signal of the sensor respectively.

Yet another advantage of the present invention is the outer members provide an option for a simple attachment of the sensor to a surface mounted package thereby eliminating output signal variability due to the attachment of sensors without outer members.

Moreover, yet another advantage of the present invention is that the electrical output signal of the accelerometer can be functionally adjusted by reducing a small amount of metalization from the top portion of the third member by laser trimming, thereby reducing the effective net length.

The present invention is specifically concerned with a method of manufacturing a surface mountable piezoceramic accelerometer, and in particular an accelerometer with adjustable sensitivity which corresponds to the inventive shape of the sensor. The preferred method involves surface mounting via a protective package to the hybrid circuit of the pacemaker. This method further provides pre-circuit attachment testing and adjustment for performance centering and yield enhancement. An alternative coupling method is also disclosed. The alternative method of mounting is by direct surface mounting of the sensor to the hybrid circuit of the pacemaker.

Other features, advantages and objects of the piezoceramic accelerometer sensor and method of manufacture of the present invention will hereinafter become more fully apparent from the following description of the drawings, which illustrate the invention.

DESCRIPTION OF THE PREFERRED EMBODIMENTS

Figure 1:
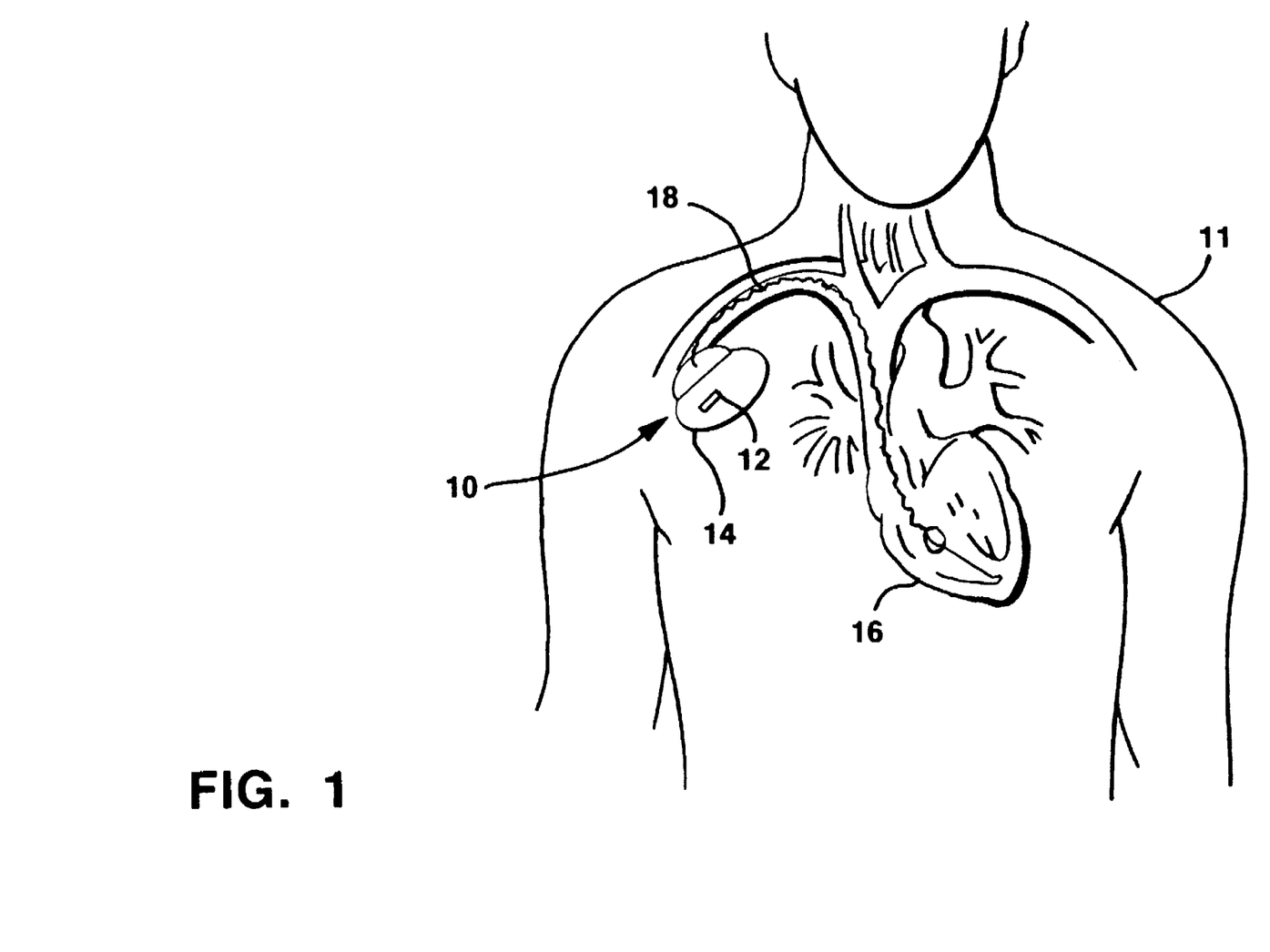
FIG. 1 is an illustration showing placement of a pacemaker in accordance with the disclosed embodiment of the invention in a patient.

Referring to FIG. 1, there is illustrated the placement of a pacemaker 10 in accordance with one embodiment of the present invention. Pacemaker 10 is shown in FIG. 1 as it would be implanted in a patient 11. The preferred embodiment of the invention includes an activity sensor 12, which is a piezoceramic accelerometer disposed on the hybrid circuit and isolated from the housing 14 of pacemaker 10. Pacemaker 10 may additionally include other sensors, such as a pressure sensor or the like implanted within heart 16 or disposed on the distal end of pacemaker lead 18.

A pacemaker which measures the physical activity of a patient by means of a piezoelectric transducer which is disposed on the housing of the pacemaker is disclosed in U.S. Pat. No. 4,485,813 to Anderson et al. and assigned to the assignee of the present invention, which patent is incorporated herein by reference in its entirety. Also in U.S. Pat. No. 5,031,615 issued to Alt as disclosed, supra, is another example of an activity-sensing cardiac pacemaker which uses an integrated miniaturized accelerometer.

It is to be understood that the present invention is not limited in scope to either single-sensor or dual-sensor pacemakers, and that other sensors besides activity and pressure sensors could be used in practicing the present invention. Nor is the present invention limited in scope to single-chamber pacemakers. A multiple-chamber (e.g., dual-chamber) pacemaker can also be used in practicing the present invention.

Figure 2:
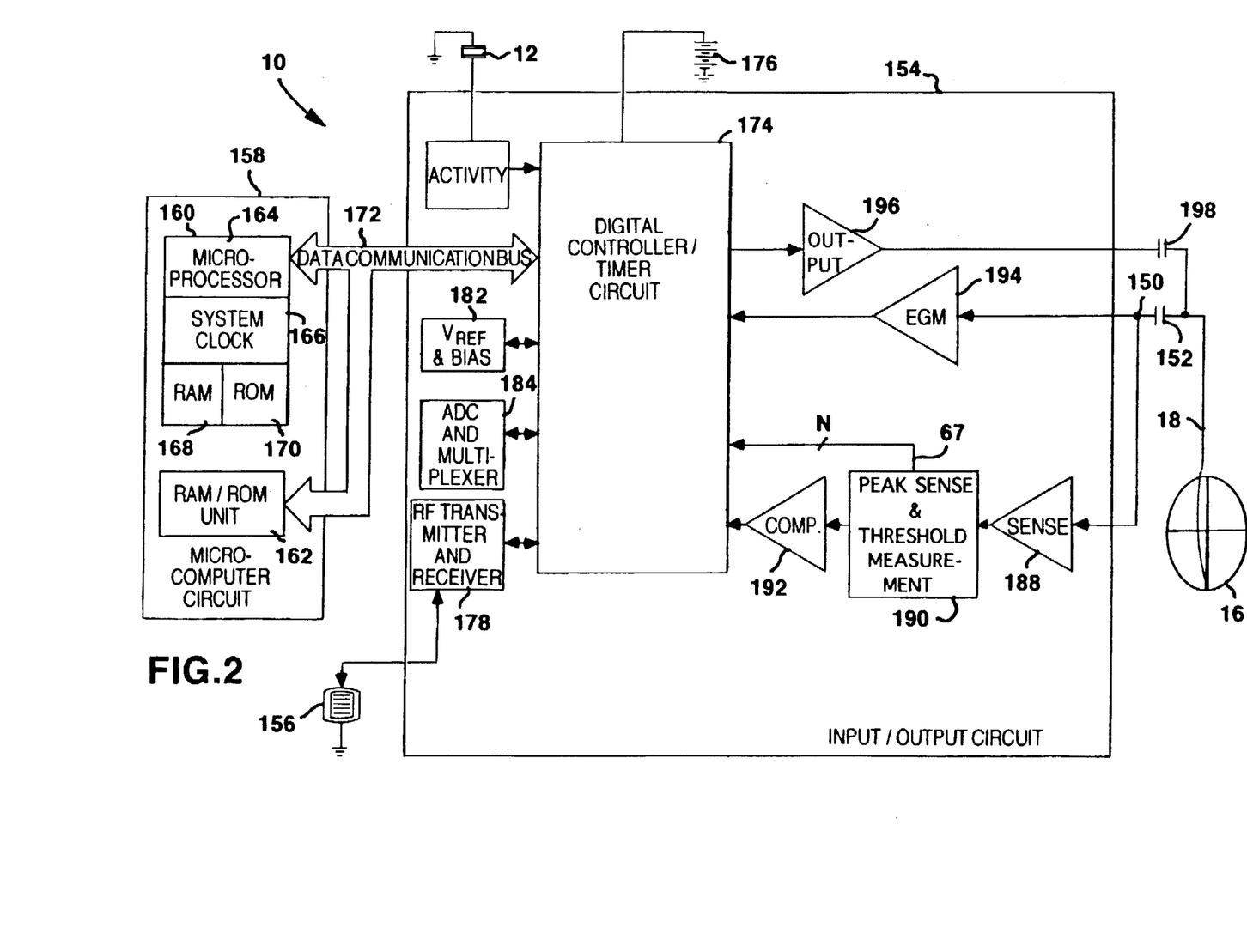
FIG. 2 is a block diagram of a pacemaker in accordance with the disclosed embodiment of the invention.

Turning now to FIG. 2, a block diagram illustrating the constituent components of a pacemaker 10 in accordance with the presently disclosed embodiment of the invention is provided. Although the present invention will be described herein in conjunction with a pacemaker 10 having a microprocessor-based architecture, it will be understood that the present invention may be utilized in conjunction with other implantable medical devices, such as cardioverters, defibrillators, cardiac assist systems, and the like.

In the illustrative embodiment shown in FIG. 2, pacemaker 10 includes an activity sensor 12, which as previously noted is a piezoceramic accelerometer bonded to the hybrid circuit inside of the pacemaker housing. Piezoceramic accelerometer sensor 12 provides a sensor output which varies as a function of a measured parameter that relates to the metabolic requirements of patient 11.

Pacemaker 10 of FIG. 2 is programmable by means of an external programming unit (not shown in the figures). One such programmer suitable for the purposes of the present invention is the Medtronic Model 9790 programmer which is commercially available and is intended to be used with all Medtronic pacemakers. The programmer is a microprocessor device which provides a series of encoded signals to pacemaker 10 by means of a programming head which transmits radio-frequency (RF) encoded signals to pacemaker 10 according to the telemetry system laid out, for example, in U.S. Pat. No. 5,312,453 issued on Jul. 7, 1992 to Wyborny et al., which is hereby incorporated by reference in its entirety. It is to be understood, however, that the programming methodology disclosed in Wyborny et al. patent is identified herein for the purposes of illustration only, and that any programming methodology may be employed so long as the desired information is transmitted to the pacemaker. It is believed that one of skill in the art would be able to choose from any of a number of available programming techniques to accomplish this task.

The programmer facilitates the selection by a physician of the desired parameter to be programmed and the entry of a particular setting for the desired parameter. For purposes of the present invention, the specifics of operation of the programmer are not believed to be important.

Pacemaker 10 is schematically shown in FIG. 2 to be electrically coupled via a pacing lead 18 to a patient's heart 16. Lead 18 includes an intracardiac electrode located near its distal end and positioned within the right ventricular (RV) or right atrial (RA) chamber of heart 16. Lead 18 can carry either unipolar or bipolar electrodes as is well known in the art. Although an application of the present invention in the context of a single-chamber pacemaker will be disclosed herein for illustrative purposes, it is to be understood that the present invention is equally applicable in dual-chamber pacemakers.

Lead 18 is coupled to a node 150 in the circuitry of pacemaker 10 through input capacitor 152. In the presently disclosed embodiment, piezoceramic accelerometer 12 is attached to the hybrid circuit inside of the pacemaker 14 (not shown in FIG. 2), as noted with reference to FIG. 1. As shown in FIG. 2, the output from piezoceramic accelerometer 12 is coupled to an input/output circuit 154.

Input/output circuit 154 contains the analog circuits for interface to heart 16, piezoceramic accelerometer 12, an antenna 156, as well as circuits for the application of stimulating pulses to heart 16 to control its rate as a function thereof under control of the software-implemented algorithms in a microcomputer circuit 158.

Microcomputer circuit 158 comprises an on-board circuit 160 and an off-board circuit 162. Unit 158 may correspond to the microcomputer circuit employed in U.S. Pat. No. 5,312,453 issued to Shelton et al. on May 7, 1994., which is hereby incorporated by reference in its entirety. On-board circuit 160 includes a microprocessor 164, a system clock circuit 166, and on-board RAM 168 and ROM 170. In the presently disclosed embodiment of the invention, off-board circuit 162 comprises a RAM/ROM unit. On-board circuit 160 and off-board circuit 162 are each coupled by a data communication bus 172 to a digital controller/timer circuit 174. Microcomputer circuit 158 may be fabricated of a custom integrated circuit device augmented by standard RAM/ROM components.

It will be understood that the electrical components represented in FIG. 2 are powered by an appropriate implantable battery power source 176, in accordance with common practice in the art. For the sake of clarity, the coupling of battery power to the various components of pacemaker 10 has not been shown in the figures.

Antenna 156 is connected to input/output circuit 154 for purposes of uplink/downlink telemetry through RF transmitter and receiver unit 178. Unit 178 may correspond to the telemetry and program logic employed in U.S. Pat. No. 4,566,063 issued to Thompson et al. on Dec. 3, 1985 or in the above-referenced Wyborny et al. patent, both of which are incorporated herein by reference in their entirety. The particular programming and telemetry scheme chosen is not believed to be important for the purposes of the present invention so long as it provides for entry and storage of values of rate-response parameters discussed herein.

A $V_{REF}$ and Bias circuit 182 generates a stable voltage reference and bias currents for the analog circuits of input/output circuit 154. An analog-to-digital converter (ADC) and multiplexer unit 184 digitizes analog signals and voltages to provide "real-time" telemetry intracardiac signals and battery end-of-life (EOL) replacement function.

The operating commands for controlling the timing of pacemaker 10 are coupled by data bus 172 to digital controller/timer circuit 174 wherein digital timers and counters are employed to establish the overall escape interval of the pacemaker, as well as various refractory, blanking, and other timing windows for controlling the operation of the peripheral components within input/output circuit 154.

Digital controller/timer circuit 174 is coupled to sensing circuitry including a sense amplifier 188, a peak sense and threshold measurement unit 190, and a comparator/threshold detector 192. Circuit 174 is further coupled to an electrogram (EGM) amplifier 194 for receiving amplified and processed signals picked up by the electrode disposed on lead 18 which signals are representative of the electrical activity of the patient's heart 16. Sense amplifier 188 amplifies sensed electrical cardiac signals and provides this amplified signal to peak sense and threshold measurement circuitry 190, which provides an indication of peak sensed voltages and the measured sense amplifier threshold voltage on multiple conductor signal path 67 to digital controller/timer circuit 174. The amplified sense amplifier signal is then provided to comparator/threshold detector 192. Sense amplifier 188 may correspond, for example, to that disclosed in U.S. Pat. No. 4,379,459 issued to Stein on Apr. 12, 1983, incorporated by reference herein in its entirety. The electrogram signal developed by EGM amplifier 194 is used on those occasions when the implanted device is being interrogated by an external programmer, not shown, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference. An output pulse generator 196 provides pacing stimuli to the patient's heart 16 through coupling capacitor 198 in response to a pacing trigger signal developed by digital controller/timer circuit 174 each time the escape interval times out, or an externally transmitted pacing command has been received, or in response to other stored commands as is well known in the pacing art. Output amplifier 196 may correspond generally to the output amplifier disclosed in U.S. Pat. No. 4,476,868 issued to Thompson on Oct. 16, 1984 also incorporated herein by reference in its entirety.

While specific embodiments of input amplifier 188, output amplifier 196, and EGM amplifier 194 have been identified herein, this is done for the purposes of illustration only. It is believed by the inventors that the specific embodiments of such circuits are not critical to the present invention so long as they provide means for generating a stimulating pulse and provide digital controller/timer circuit 174 with signals indicative of natural and/or stimulated contractions of the heart.

Figure 3:
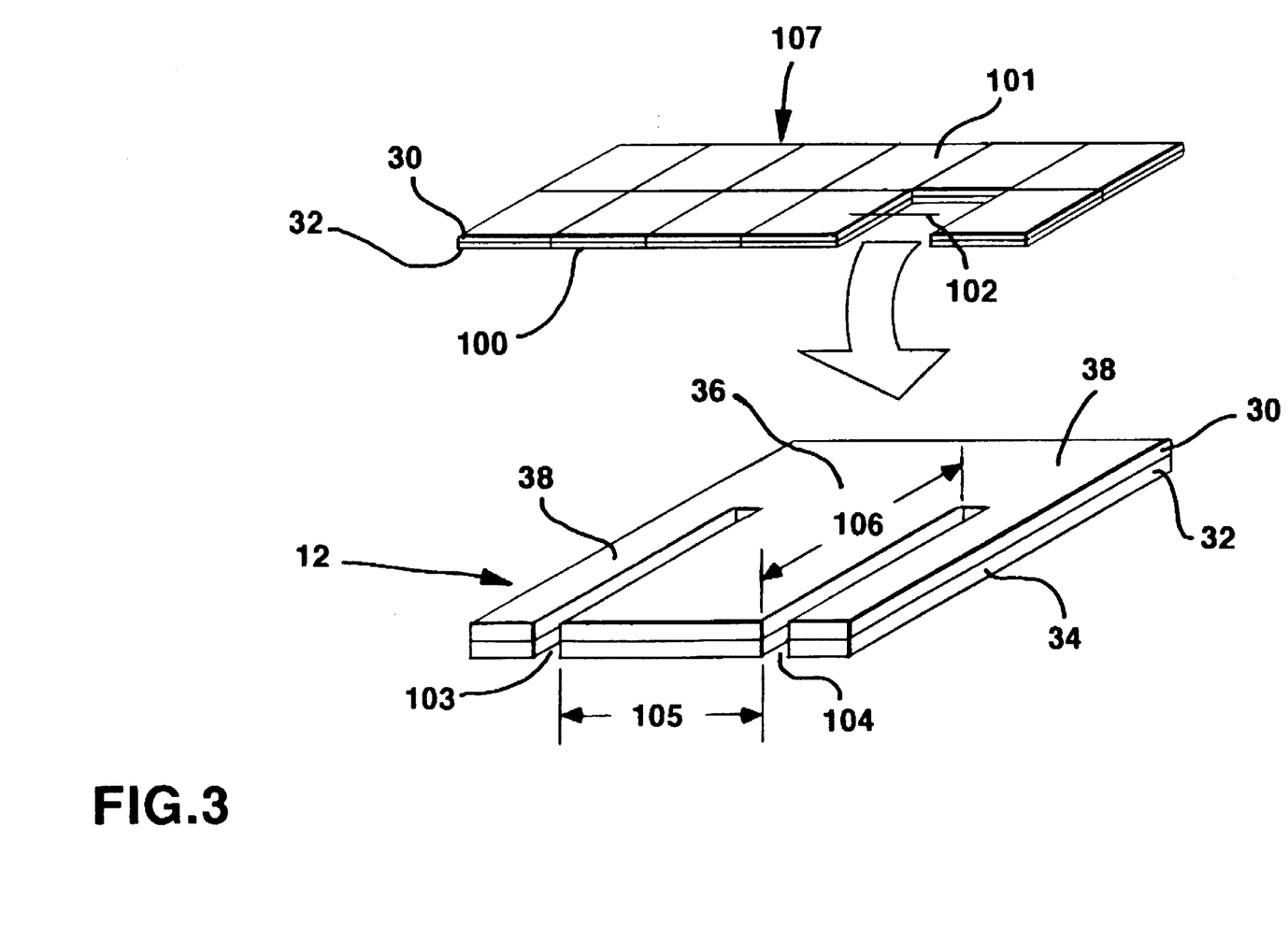
FIG. 3 is a perspective view of a bimorph accelerometer in accordance with the disclosed embodiment of the invention.
Figure 4A:
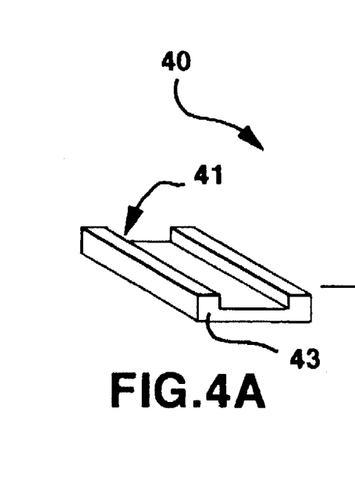
FIGS. 4A–4E show a diagrammatic representation of the process steps involved in an exemplary embodiment of the method of the present invention.
Figure 4B:
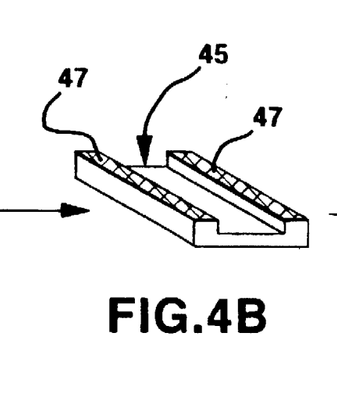
Figure 4C:
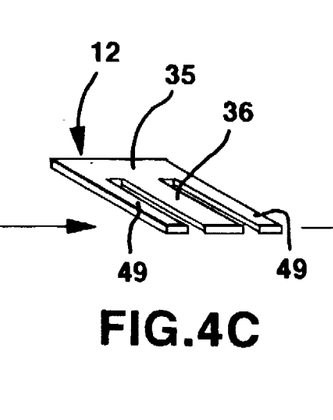
Figure 4D:
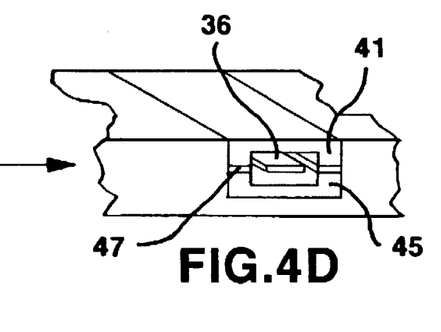
Figure 4E:
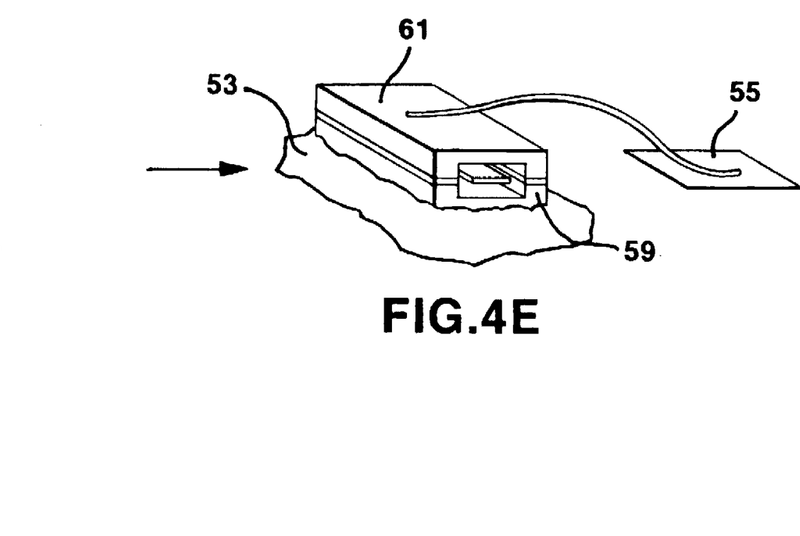

FIG. 3 illustrates the manufacture of a piezoceramic accelerometer. The two sheets of piezoelectric material 30 and 32 are bonded together to form a bimorph with a platinum metal 34 between. This structure is then co-fired and subsequently nickel electrode layers are 100 and 101 plated on the upper and lower surface of the bimorph sheet. Next, the piezoelectric sheet is poled by conventional means to yield piezoelectric properties, that is the electrical axes are set during polling to established the orientation of the electrical properties. The sheet 107 is then cut up into smaller rectangular elements with a ceramic cutting saw (not shown in the figures). The process of manufacturing piezoelectric material is well known and believed that one skilled in the art would be able to accomplish such a task.

Figure 5A:
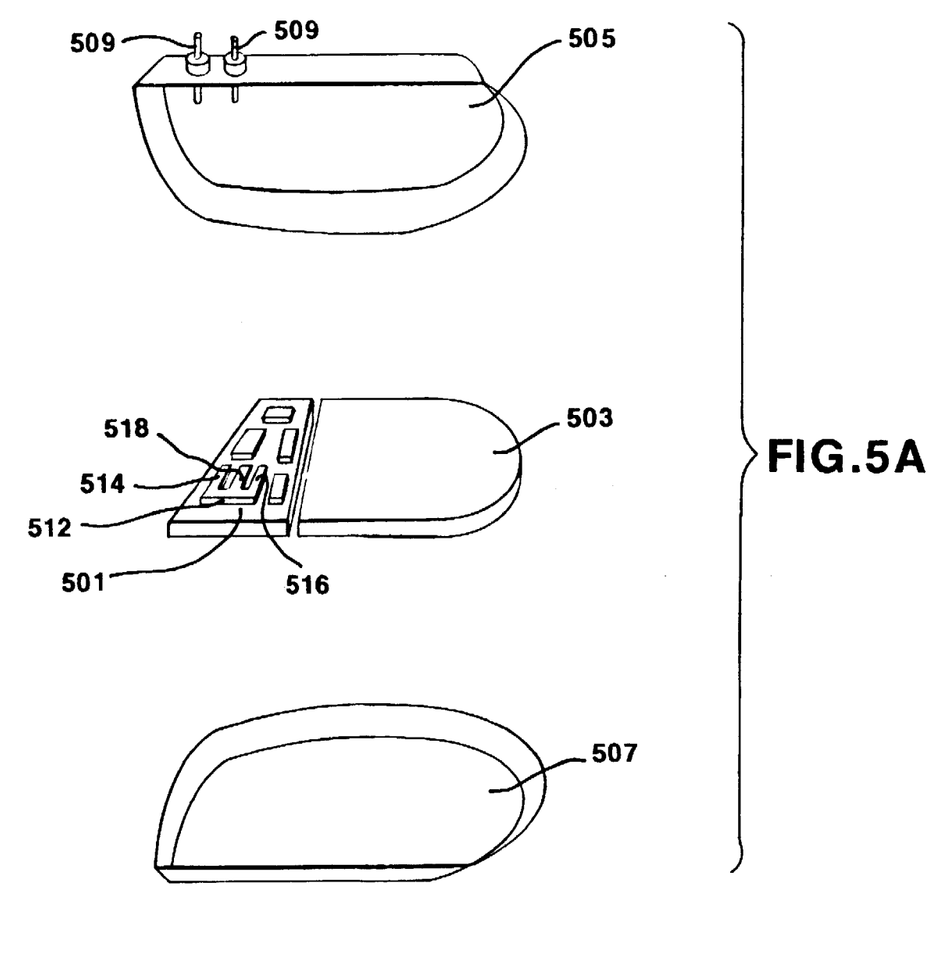
FIGS. 5A and 5B show is an exploded perspective view of an implantable medical device and the electronics which are hermetically sealed by the device shields.

Next, the step of defining active area 36, the cantilever beam, and inactive areas 38 which are employed to couple the accelerometer to the pacemaker hybrid circuit is performed. FIG. 3 shows a piezoceramic sensor 102. Incisions 103 and 104 are made which separate the inactive and active areas of the sensor. The incisions into the piezoelectric material are also employed to define the sensitivity of the sensor by controlling the resulting beam width 105 and length 106. The accelerometer in FIG. 3 is then surface mounted onto the hybrid circuit as shown in FIG. 5.

Turning to FIG. 5, a finished medical device (e.g.a cardiac pacemaker) is formed by mounting one or more feed throughs 509 to one or more of the shield halves 505 and 507, enclosing the internal electronics 501, (e.g. pulse generator circuitry) including a piezoelectric accelerometer 512, and the battery cell 503 within the shield halves 505 and 507, coupling the battery 503 to the circuitry, coupling the circitry to the feedthroughs 509 and subsequently laser welding the shield halves together along their edges to form a substantially hermetic enclosure. A molded plastic connector block assembly (not illustrated) containing electrical connectors for attachment to the feedthroughs 509 is typically installed thereafter.

In FIG. 5, the outer members 514 and 516 of the sensor permit direct attachment to the hybrid circuit during final assembly by employing either a solder reflow or a conductive epoxy film, which provides an electrical connection to the bottom side electrode, thereby elevating the sensor from the hybrid substrate surface and providing satisfactory vibration space for the center member 518 to move in a perpendicular arc relative to the planar surface of the sensor. Furthermore, the attachment process, supra, eliminates the variability of the electrical output signal by providing a consistent attachment means of the accelerometer to the pacemaker hybrid.

Moreover, the electrical output signal of the accelerometer can be functionally adjusted by reducing a small amount of metalization from the top portion of the center member by conventional laser trimming, (not shown in the figures), thereby reducing the effective net length.

Referring now to FIG. 4, the outer members 49 of the accelerometer 12 are employed to mount the accelerometer within a low cost protective package in accordance with the preferred embodiment of the present invention is diagrammatically illustrated. In FIG. 4A, a Ni/Au plated lid 41 is formed into a "U" shape 43 to allow clearance for perpendicular movement of the center member (cantilever beam) 36. The lids 41 and 45 have been formed to contact only the outer members of the "M" in 12. After the metal housings are made and plated, a conductive epoxy 47 is added to lid 45, which contacts the outer members 49 of the accelerometer 12 in FIG. 4C. The epoxy 47 forms an electrical contact between the nickel plated surfaces of the piezoelectric accelerometer and the metal housing. The conductive epoxy also provides a mechanical bond, which holds all three pieces together and is cured under pressure in FIG. 4D, wherein the latter curing step is conventional to the present art. The center member 36 (active area of the accelerometer) of the accelerometer 12 is isolated from the packaging assembly. Once the assembly process 40 is complete as illustrated in FIG. 4E the device defines an accelerometer component which can be tested and characterized prior to coupling one terminal 59 of the device with solder 53 to the hybrid, (not shown in the figures), and electrically coupling by an ultrasonic wire bond process the other terminal 61 to the hybrid via a wire bond 55. Hence, this protective packaging process enhances manufacturing yields by obviating the variability of the output signal by providing a consistent attachment means of the accelerometer to the protective package.

Moreover, the output signal may be augmented to by a twisting movement at the base of the sensor 35 which adds to the output signal generated by the center member 36. The fashion by which the outer members of the sensor are bonded may add to the output signal or subtract from the output signal. For example, if conductive epoxy is applied from the base of the sensor to the opposite end of the base of the sensor along the outer members, this bonding method will reduce the twisting of the sensor at the base, hence subtract from the overall output signal. As the epoxy is removed from the base towards the opposite end of the base of the sensor along the outer members, this bonding method will increase the twisting of the sensor at the base, hence add to the overall output signal.

While only a single embodiment of the invention has been illustrated and described, it is not intended to be limited by the aforementioned embodiment of the invention and the following alternative embodiment should be considered.

Figure 5B:
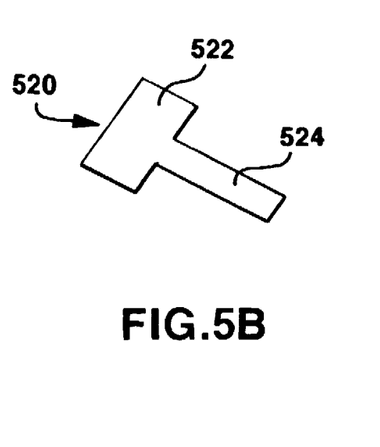

A method of manufacturing a sensor for a medical device by providing a bimorphic piezoceramic substrate and sculpturing a first member and second member from the piezoceramic substrate, wherein the first and second members are integral and define a sensor 520 for a medical device in FIG. 5B. The first member 522 is employed to couple the sensor within the medical device, and the second member 524 defines the active area of said sensor, which is also known as the cantilever beam of the sensor. Both members can be positioned to form a substantially "T" shape as shown in FIG. 5B. Note that the accelerometer 512 in FIG. 5A can be replaced with piezoelectric sensor 520 in FIG. 5B.

Although specific embodiments of the invention have been set forth herein in some detail, it is to be understood that this has been done for the purposes of illustration only, and is not to be taken as a limitation on the scope of the invention as defined in the appended claims. It is to be understood that various alterations, substitutions, and modifications may be made to the embodiment described herein without departing from the spirit and scope of the appended claims.

We claim:

1. A cardiac pacemaker, comprising:

means for generating stimulus pulses at a rate;

a sensor means for sensing a patient's activity, wherein said sensor means generates an output signal indicative of said patient's activity;

means for processing said output signal and for controlling said rate of said stimulus pulses generated as a function of said patient's activity;

means for mounting said sensor means inside said pacemaker;

said sensor means comprising:

a first generally planar structure;

a second generally planar structure;

said first generally planar structure and said second generally planar structure being bonded together to form a generally planar substrate;

said substrate having a leg portion having a longitudinal length formed therein, wherein first and second ends define the longitudinal length of the leg portion, lateral portions extend laterally outwardly from said first end, said mounting means are attached only to said lateral portions, and said second end of said leg portion is spaced apart from said mounting means and deflectable in a plane generally perpendicular to said substrate.

2. A pacemaker according to claim 1, wherein the leg portion is disposed between two outwardly disposed legs, each outwardly disposed leg having first and second ends, each of the first ends of the outwardly disposed legs being attached to and contiguous with the lateral portions.

3. A pacemaker according to claim 1 or claim 2, wherein said leg portion generates said output signal of said sensor.

4. A pacemaker according to claim 1 or claim 2, wherein said outwardly disposed legs define an inactive area of said sensor.

5. A method of manufacturing a sensor for an implantable medical pacemaker, comprising:

providing a first planar structure;

providing a second planar structure;

bonding said first and second planar structures to form a substrate;

sculpturing a first leg from said substrate;

sculpturing a second leg from said substrate;

sculpturing a third leg from said substrate, said third leg having a longitudinal length defined by first and second ends, a lateral width, and a thickness less than said length and said width, said third leg being disposed between said first and second legs, the first end being contiguous with and attached to lateral portions extending outwardly to said first and second legs, said sensor for said pacemaker being formed by said sculpturing steps; and bonding said sensor within said pacemaker such that said third leg is free to deflect perpendicular to a plane formed by said first and second legs of said sensor.

6. The method according to claim 5, wherein said bonding step further comprises the step of adjusting said sensor output voltage of said sensor by decreasing said bonding area of said first and second legs within said pacemaker.

7. A method of employing a protective package for mounting a sensor within an implantable pacemaker, comprising:

providing a top portion with a recess;

providing a bottom portion with a recess;

providing said sensor having a shape defined by three integral legs, said third leg disposed between a first and second leg, and having a longitudinal length, a lateral width, and a thickness less than said length and said width;

positioning said sensor between said top and bottom portions to couple said first and second legs to said top and bottom portions such that said third leg is free to move within said recess perpendicular to a plane formed by said first and second legs of said sensor; and bonding said sensor within said pacemaker.

8. The method according to claim 7, wherein said step of positioning said sensor between said top and bottom portions comprises means for generating an output signal by deforming said third leg.

9. A cardiac pacemaker, comprising a pacing pulse generator, a piezoelectric activity sensor mounted to an internal surface of said pacemaker and providing an output signal indicative of a patient's level of activity, and means responsive to said output signal for triggering said pulse generator to produce pacing pulses at a rate correlated to said patient's level of activity, wherein said sensor comprises;

a generally planar sheet of piezoelectric material having a leg portion with a longitudinal length extending between first and second ends, a lateral width, a thickness less than said length and said width, and portions extending laterally adjacent said first end of said leg portion, said laterally extending portions mounted to said internal surface, said second end of said leg portion spaced from said internal surface and deflectable in a plane generally perpendicular to said generally planar sheet.

10. A pacemaker according to claim 9, wherein said length of said leg portion exceeds the width of said leg portion.

11. A pacemaker according to claim 9 wherein said laterally extending portions in turn comprise longitudinally extending portions extending parallel to said leg portion and spaced therefrom.

12. A pacemaker according to claim 9 wherein said generally planar sheet of piezoelectric material is provided with two longitudinally extending cuts through the thickness thereof, separating said second end of said leg portion from said laterally extending portions.

13. A pacemaker according to claim 9 or claim 10 or claim 11 or claim 12 wherein said generally planar sheet of piezoelectric material comprises two generally planar layers of piezoelectric material bonded to one another to form a bimorph.

14. A pacemaker according to claim 13 wherein said generally planar sheet of piezoelectric material is attached to said internal surface only at locations on said laterally extending portions which are spaced laterally outward from said leg portion.

15. A pacemaker according to claim 9 or claim 10 or claim 11 or claim 12 wherein said generally planar sheet of piezoelectric material is attached to said internal surface only at locations on said laterally extending portions which are spaced laterally outward from said leg portion.

16. A pacemaker according to claim 15 wherein said generally planar sheet of piezoelectric material comprises two generally planar layers of piezoelectric material bonded to one another to form a bimorph.

17. A pacemaker according to claim 9 or claim 10 or claim 11 or claim 12 further comprising an enclosure for said generally planar sheet of piezoelectric material, comprising a first enclosure member, said first enclosure member having raised edges and a longitudinally extending central channel located between said raised edges, and wherein said laterally extending portions of said generally planar sheet of piezoelectric material are mounted to said raised edges with said leg portion located over said central channel.

18. A pacemaker according to claim 17, further comprising a second enclosure member having downward extending edges and a longitudinally extending central channel located between said edges, wherein said second enclosure member is mounted to said first enclosure member with said central channel of said second enclosure member located over said leg portion of said generally planar sheet of piezoelectric material.

19. A pacemaker according to claim 18, wherein said laterally extending portion of said generally planar sheet of piezoelectric material are mounted between said raised and downward extending edges of said first and second enclosure members.

20. A cardiac pacemaker, comprising a pacing pulse generator, a piezoelectric activity sensor mounted to an internal surface of said pacemaker and providing an output signal indicative of a patient's level of activity, and means responsive to said output signal for triggering said pulse generator to produce pacing pulses at a rate correlated to said patient's level of activity, wherein said sensor comprises:

a generally planar sheet of piezoelectric material having a leg portion with a longitudinal length extending between first and second ends;

lateral portions extending laterally outwardly from said first end of said leg portion;

wherein said internal surface is attached only to said lateral portions and said second end of said leg portion is spaced apart from said internal surface and deflectable in a plane generally perpendicular to said generally planar sheet.

* * * * *

UNITED STATES PATENT AND TRADEMARK OFFICE
CERTIFICATE OF CORRECTION

PATENT NO. : 5,674,258
DATED : Oct. 7, 1997
INVENTOR(S) : Mark E. Henschell et al.

It is certified that error appears in the above-identified patent and that said Letters Patent is hereby corrected as shown below:

Abstract (P1)  "Disclosed are method" to be changed to "Disclosed are a method"

Signed and Sealed this

Fourth Day of January, 2000

Attest:

*Attesting Officer*    *Acting Commissioner of Patents and Trademarks*